United States Patent [19]

Nagata et al.

[11] 4,336,381

[45] Jun. 22, 1982

[54] 5-FLUOROURACIL DERIVATIVES

[75] Inventors: Wataru Nagata, Nishinomiya; Susumu Kamata, Takarazuka, both of Japan

[73] Assignee: Shionogi & Co., Ltd., Osaka, Japan

[21] Appl. No.: 203,363

[22] Filed: Nov. 3, 1980

[30] Foreign Application Priority Data

Nov. 8, 1979 [JP] Japan .............................. 54/145131

[51] Int. Cl.³ .......................................... C07D 239/55
[52] U.S. Cl. .................................................. 544/313
[58] Field of Search ......................................... 544/313

[56] References Cited

U.S. PATENT DOCUMENTS 4,124,765 11/1978 Kurono et al. ...................... 544/313
4,267,326 5/1981 Ozaki et al. ......................... 544/313

Primary Examiner—Paul M. Coughlan, Jr.
Attorney, Agent, or Firm—Wenderoth, Lind & Ponack

[57] ABSTRACT

Orally administrable 5-fluorouracil derivatives of the general formula:

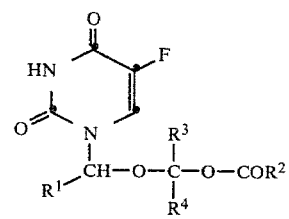

[wherein $R^1$ is aryl or substituted aryl; $R^2$ is acyclic or cyclic alkyl, adamantyl, aryl or substituted aryl; $R^3$ and $R^4$ are the same or different, each representing hydrogen atom or lower alkyl] effective against malignant tumors.

13 Claims, 1 Drawing Figure

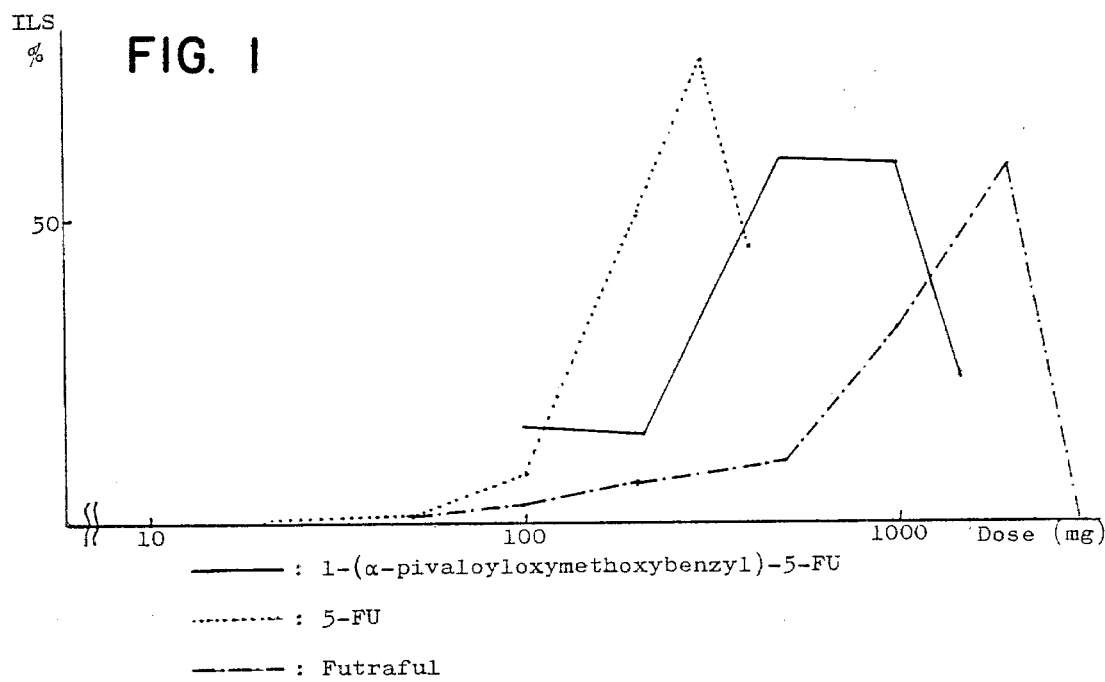

5-FLUOROURACIL DERIVATIVES

This invention relates to antitumor agents. More particularly, this invention relates to 5-fluorouracil derivatives having antitumor action.

BACKGROUND OF THE INVENTION

5-Fluorouracil (hereinafter abbreviated to as 5-FU) has been used clinically in treatment of malignant tumors, for example, carcinoma, sarcoma, skin cancer, cancer of the digestive organs, cancer of the breast. 5-FU, however, shows serious adverse reactions such as nausea, alopecia, diarrhea, stomatitis, leukocytic thrombocytopenia, anorexia, pigmentation, edema, general fatigue, etc., in application over a long period of days, and it is difficult to administer orally because of its strong toxicity. Recently, the occurrence of and death rate owing to malignant tumors show a tendency to increase, and it is desired to develop antitumor agents for which the activity is strong but which are less toxic, and which can be orally administered. In order to achieve the above purpose, chemical modification of a powerful antitumor agent, 5-FU which unfortunately has strong toxicity has been attempted extensively. Representatives of the modified 5-FU derivatives already known are 1-(2-tetrahydrofuryl)-5-fluorouracil [trademark: Ftorafur (Taiho Yakuhin); Japanese Unexamined Patent Publication Nos. 50-50383, 50-50384, 50-64281, 51-146482 and 53-84981], and 1-carbamoyl-5-fluorouracil [Mitsui Seiyaku; Japanese Unexamined Patent Publication No. 50-148365].

DETAILED DESCRIPTION OF THE INVENTION

The compounds of this invention are represented by the general formula (I):

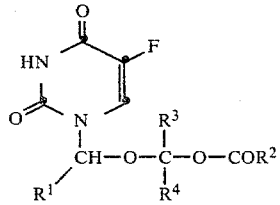

[wherein $R^1$ is aryl or substituted aryl; $R^2$ is acyclic or cyclic alkyl, adamantyl, aryl or substituted aryl; and $R^3$ and $R^4$ are the same or different, each representing hydrogen atom or lower alkyl].

In the above definition, lower alkyl means $C_1$ to $C_5$ alkyl, for example, methyl, ethyl, propyl, isopropyl, butyl, isobutyl, t-butyl, pentyl, isopentyl, neopentyl, and t-pentyl. Acyclic alkyl means $C_1$ to $C_{30}$ straight or branched chain alkyl, preferably $C_1$ to $C_{10}$ alkyl, for example, in addition to the above mentioned lower alkyl, hexyl, isohexyl, heptyl and octyl. Cyclic alkyl means $C_3$ to $C_{11}$ 3–6 membered cyclic alkyl, for example, cyclopropyl, cyclobutyl, cyclopentyl, and cyclohexyl, which may be substituted by the above mentioned lower alkyl. The definition of cyclic alkyls also include those in which the cycloalkyl is attached to the carbonyl group through the above mentioned lower alkyl, for example, cyclopropylmethyl and cyclohexylethyl. Aryl means $C_6$ to $C_{10}$ aryl, for example, phenyl, indanyl, and naphthyl, which may have one or more of substituents such as halogen (e.g. fluoro, chloro, bromo, iodo), $C_1$ to $C_5$ alkyl (e.g. methyl, ethyl, propyl, isopropyl), $C_1$ to $C_5$ haloalkyl (e.g. trifluoromethyl), $C_1$ to $C_5$ alkoxy (e.g. methoxy, ethoxy, propoxy, isopropoxy), nitro, cyano, carboxy or the like.

Representative of the compounds (I) are:
1-(α-acetoxymethoxybenzyl)-5-fluorouracil,
1-(α-acetoxymethoxy-2-fluorobenzyl)-5-fluorouracil,
1-(α-acetoxymethoxy-4-fluorobenzyl)-5-fluorouracil,
1-(α-propionyloxymethoxybenzyl)-5-fluorouracil,
1-(α-propionyloxymethoxy-2-fluorobenzyl)-5-fluorouracil,
1-(α-octanoyloxymethoxy-2-fluorobenzyl)-5-fluorouracil,
1-(α-octanoyloxymethoxy-4-fluorobenzyl)-5-fluorouracil,
1-[α-(1-adamantanoyloxymethoxy)benzyl]-5-fluorouracil,
1-[α-(1-adamantanoyloxymethoxy)-4-fluorobenzyl]-5-fluorouracil,
1-(α-pivaloyloxymethoxybenzyl)-5-fluorouracil,
1-[α-(2,2-dimethyloctanoyloxymethoxy)benzyl]-5-fluorouracil, and
1-(α-pivaloyloxymethoxy-4-carboxybenzyl)-5-fluorouracil.

The compounds (I) may readily be prepared from the readily available starting materials as shown in the following reaction scheme.

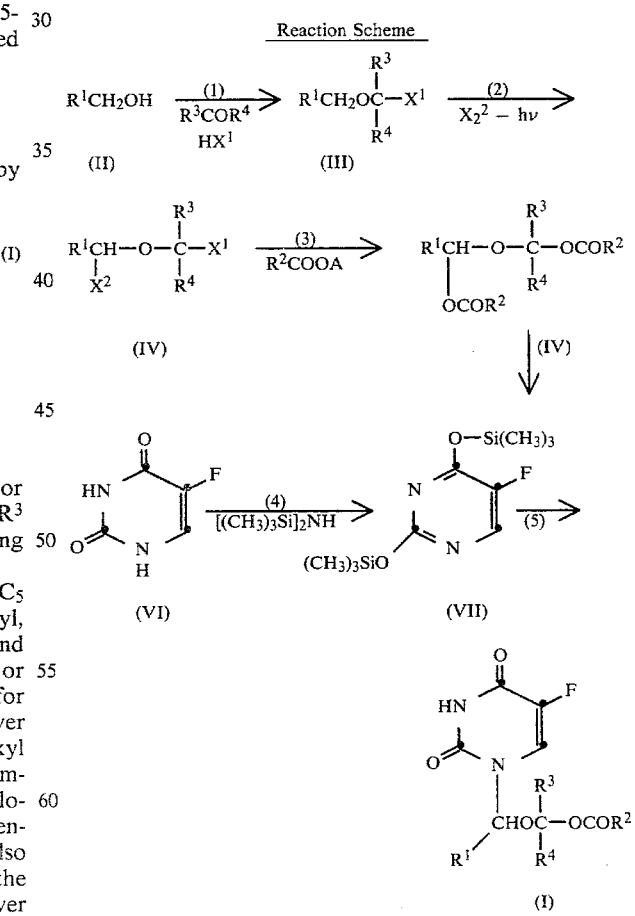

[wherein $R^1$, $R^2$, $R^3$ and $R^4$ each has the same meaning as mentioned above; $X^1$ and $X^2$ are the same or different, each representing halogen atom; and A is alkali metal.]

The above mentioned steps (1) to (5) can be achieved by the well-known method as follows:

Step (1)

The starting alcohols (II) are allowed to react with aldehydes or ketones in the presence of a hydrogen halide to give the ether compounds (III). The aldehydes or ketones may be used in an amount equal or in excess of, preferably 1 to 3 equivalents, more preferably 1 to 2 equivalents to the alcohol (II).

When both of $R^3$ and $R^4$ are hydrogen, formaldehyde may be employed, but more preferably it is appropriate to use formalin or polymeric formaldehydes such as paraformaldehyde.

The reaction is preferably carried out in an inert solvent (e.g. benzene, toluene, xylene, methylene chloride, chloroform). The reaction proceeds well under cooling or at room temperature and is complete within a period of several hours. The reaction can be accelerated under warming.

Step (2)

The ether compounds (III) are allowed to react with a halogen under irradiation of light to give the dihalogenated compounds (IV). This reaction which is halogen radical reaction caused by light can be carried out preferably in the above mentioned inert solvent under irradiation by a tungsten lump, mercury lump or the like light sources.

Step (3)

The dihalogenated compounds (IV) are allowed to react with alkali metal salts of carboxylic acids in the presence of a catalyst to give the dicarboxy compounds (V). As for the catalyst, cyclic polyethers such as dicyclohexyl-18-crown-6, dicyclohexyl-24-crown-8, diphenyl-18-crown-6, diphenyl-15-crown-5, and the like may preferably be employed.

The reaction is also carried out in the above mentioned solvent. The reaction proceeds well at room temperature. Preferably, the reaction may be carried out under refluxing at elevated temperatures for a period of several hours.

The steps (1) to (3) may be operated successively. The resulting compounds (V) are novel.

Step (4)

5-FU (VI) is allowed to react with hexamethyldisilazane to give the bis-trimethylsilyl compound (VII). The compound (VII) which is used as starting material for modification of 5-FU has been described in Japanese Unexamined Patent Publication Nos. 50-50383 and 50-50384.

Step (5)

In this step, the bis-trimethylsilyl compound (VII) is condensed with the novel dicarboxy compounds (V). The reaction is preferably carried out in the presence of a catalyst such as Lewis acid (e.g. aluminium chloride, stannic chloride, titanium chloride, borontrifluoride etherate, magnesium chloride, mercury (II) chloride, trimethylsilyl trifluoromethanesulfonate, trimethylsilyl butanesulfonate). The preferred catalyst is stannic chloride. After the completion of the reaction, the reaction mixture is worked up with an aqueous alkali solution of sodium carbonate, sodium hydrogen-carbonate or potassium hydroxide to give the objective 5-FU derivatives (I).

The compounds (I) have an excellent antitumor action. For example, the activity of 1-(α-pivaloyloxymethoxybenzyl)-5-fluorouracil is shown as follows:

Test Method

Ascites cells ($10^5$) of mouse leukemia L 1210 was diluted with a physiological salt solution and intraperitoneally administered to $BDF_1$ mice of 5 weeks age. Ten mice were employed in a control group and 7 to 8 mice were employed in a test group. The test compound was orally administered to the test group successively for 5 days.

Effect

From the average survival days in each administered group and control group, the increase of lifespan (ILS) was calculated according to the following expression.

$$ILS(\%) = \frac{\text{(Average survival days in administered group)} - \text{(Average survival days in control group)}}{\text{Average survival days in control group}} \times 100$$

From the dosage or maximum ILS value (maximum effective dose) and that of 30% ILS value (minimum effective dose), chemotherapeutic index (CI) was calculated according to the following expression. The higher value indicates the higher safety.

$$CI = \frac{\text{maximum effective dose (mg/kg)}}{\text{minimum effective dose (mg/kg)}}$$

(Result)

TABLE 1

| dose (mg × days) | ILS value (%) of each drug | | |
|---|---|---|---|
| | 5-FU | Futraful ® | Compound (A) |
| 0 × 5 | — | — | — |
| 4 × 5 | 0 | 1 | — |
| 10 × 5 | 1 | 1 | — |
| 20 × 5 | 8 | 3 | 16 |
| 40 × 5 | 51 | 6 | 15 |
| 60 × 5 | 77 | — | — |
| 80 × 5 | 46 | — | — |
| 100 × 5 | — | 10 | 61 |
| 200 × 5 | — | 32 | 60 |
| 300 × 5 | — | — | 24 |
| 400 × 5 | — | 60 | — |
| 600 × 5 | — | 1 | — |

TABLE 2

| Drug | CI value of each drug | | |
|---|---|---|---|
| | 5-FU | Futraful ® | Compound (A) |
| maximum effect dose (mg/kg) | 300 | 2,000 | 900 |
| minimum effect dose (mg/kg) | 150 | 1,000 | 300 |
| CI | 2 | 2 | 3 |

The relationship between total dosage and ILS value is illustrated by FIG. 1.

As seen from the above table and FIG. 1, the compounds of this invention show an excellent antitumor action, and may be administered orally to human or animals. Furthermore, it is seen from the dose-response relationship curve that the dosage of the compounds (I) is variable because of the low toxicity of (I) and wide range of the effective dose.

The compounds (I) of this invention can also be administered parenterally to human or animals; oral administration, however, is preferred. For example, the compounds (I) are mixed with diluent (e.g. starch, sugar, lactose, calcium carbonate, kaolin), lubricant (e.g. stearic acid, sodium benzoate, boric acid, silica, polyethylene glycol), and other pharmaceutically acceptable additives to formulate orally administrable powder, tablets, granules, capsules, troches, dry syrup, and the like. Alternatively, the compounds (I) may be dissolved or suspended in a suitable solvent for injection (e.g. distilled water for injection, ethanol, glycerin, propylene glycol, olive oil, peanut oil) and may be administered intravenously, intramuscularly or subcutaneously. In preparations for injection, the compounds (I) may be contained in ampoules in a form of solution or suspension; it is preferred to place the compounds (I) in ampoules or vials in a form of crystals, powder, microcrystals, lyophilizate, and the like and dissolve immediately before using. Stabilizing agents may be added.

When used for treatment of tumors, ordinarily the compounds (I) may be administered orally to an adult at a single or divided doses of 500 mg to 10 g 1 or 3 times a day. But it is preferred to optionally increase or decrease the dosage according to the age of patients, condition of disease, anamnesis, or the like.

The following examples are provided to further illustrate this invention.

EXAMPLE I - 1

Preparation of α-acetoxymethoxybenzyl alcohol acetate

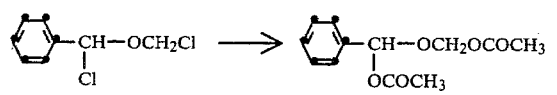

To dry benzene (200 ml) are added chloromethyl α-chlorobenzyl ether (19.1 g; 0.1 mole) [prepared in the manner described in Chemische Berichte 89, 723 (1956)], potassium acetate (2.9 g; 0.3 mole) and dicyclohexyl-18-crown-6 (500 mg), and the mixture is stirred for 2 hours under refluxing with stirring. After cooling, the insoluble materials are filtered off and washed with benzene. The filtrate and the washings are combined and concentrated under reduced pressure. The residue is distilled to give the title compound (13.2 g; yield 57%). bp. 105°–106° C./3 mmHg NMR: δ(CDCl$_3$) 2.00(s,3H), 2.10(s,3H), 5.47(s,2H), 6.87(s,1H), 7.37(5H).

EXAMPLES I - 2 to 11

The following compounds are prepared in the same manner as Example I - 1.

$$R^1-CHOC-OCOR^2$$ with $R^3$, $R^4$, $OCOR^2$ substituents

| # | R$^1$ | R$^2$ | R$^3$ | R$^4$ | Yield (%) | boiling point |
|---|---|---|---|---|---|---|
| 2 | (2-F-phenyl) | CH$_3$— | H | H | 83.4 | 108–115° C./10 mmHg |
| 3 | (4-F-phenyl) | " | " | " | 65.8 | 110–120° C./5-6 mmHg |
| 4 | (2-F-phenyl) | C$_2$H$_5$— | " | " | 63 | 124–131° C./3 mmHg |
| 5 | (2-F-phenyl) | " | " | " | 85.1 | 125–128° C./10 mmHg |
| 6 | (2-F-phenyl) | CH$_3$(CH$_2$)$_6$— | " | " | 54.4 | oily product |
| 7 | (4-F-phenyl) | " | " | " | 60.0 | " |
| 8 | (phenyl) | adamantyl | " | " | 99 | " |
| 9 | (4-F-phenyl) | " | " | " | 39 | " |
| 10 | (phenyl) | (CH$_3$)$_3$C— | " | " | 69 | 140–144° C./3 mmHg |
| 11 | (phenyl) | CH$_3$(CH$_2$)$_5$C(CH$_3$)$_2$— | " | " | 75.3 | oily product |

EXAMPLE II

Preparation of 2,4-di-(trimethylsilyloxy)-5-fluoropyrimidine

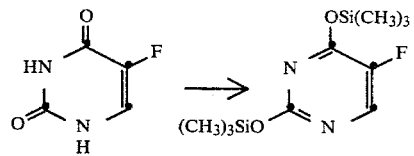

A suspension of 5-fluorouracil (32.5 g; 0.25 mole) in hexamethyldisilazane (d=0.765; 79 ml; 1.5 equivalents) is refluxed under heating at 150° C. with stirring for 3 hours and distilled in vacuo to give the title compound (63.8 g; yield 93%). bp. 83°–84° C./3 mmHg.

EXAMPLE III - 1

Preparation of 1-(α-acetoxymethoxybenzyl)-5-fluorouracil

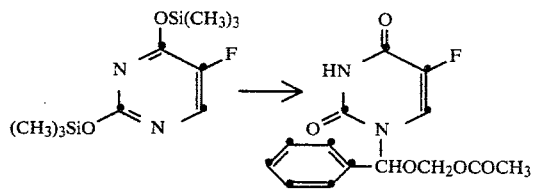

A solution of α-acetoxymethoxybenzyl alcohol acetate (1.43 g; 6 mmoles) prepared in Example I - 1 and 2,4-di-(trimethylsilyloxy)-5-fluoropyrimidine (1.37 g; 5 mmoles) in dry acetonitrile (25 ml) is cooled at 0° C. Stannic chloride (d=2.26; 0.58 ml; 5 mmoles) is added thereto, and the mixture is stirred at 0° C. for 30 minutes, then mixed with sodium hydrogencarbonate (2.52 g; 30 mmoles) and water (2.5 ml), and vigorously stirred at 0° C. The insoluble materials are filtered off and washed with acetonitrile and methylene chloride. The organic layer is washed with an aqueous saturated solution of sodium hydrogencarbonate and then with saturated brine, dried over magnesium sulfate, and evaporated. The residue is chromatographed on a column of silica gel and eluted with benzene-ethyl acetate (2:1). The eluate is recrystallized from ether to give the title compound (0.88 g; yield 57%). mp. 108°–109° C.

Elemental Analysis:
Calcd. (%) (for $C_{14}H_{13}O_5N_2F$): C, 54.54; H, 4.25; N, 9.09. Found (%): C, 54.26; H, 4.26; N, 9.15.
IR: $\nu_{max}^{CHCl_3}$ 3380, 1755, 1728, 1710, 1637 cm$^{-1}$.
NMR: $\delta(CDCl_3)$ 2.03(s,3H), 5.53(s,2H), 7.15(d, J=6 Hz, 1H), 7.20(s,1H), 7.43(5H), 9.5–11.2(br1H).

EXAMPLES III - 2 to 11

The following compounds are prepared in the same manner as Example III-1.

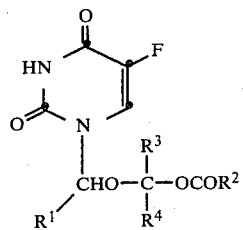

| No. | R$^1$ | R$^2$ | R$^3$ | R$^4$ | Yield (%) | mp (°C.) | Elemental Analysis | IR: $\nu_{max}^{CHCl_3}$(cm$^{-1}$) | NMR:$\delta^{CDCl_3}$ |
|---|---|---|---|---|---|---|---|---|---|
| 2. | (2-F-phenyl) | CH$_3$— | H | H | 63 | 116–118 | Calcd (for $C_{14}H_{12}O_5N_2F_2$) C, 51.54; H, 3.71; N, 8.59; F, 11.65. Found C, 51.67; H, 3.95; N, 8.53; F, 11.78. | 3380,1758, 1730,1726, 1674. | 2.03(s,3H),5.53(s,2H), 6.87–7.83(6H),10.47 (br,1H). |
| 3. | (4-F-phenyl) | " | " | " | 60 | 115–118 | Calcd (for $C_{14}H_{12}O_5N_2F_2$) C, 51.54; H, 3.71; N, 8.59; F, 11.65. Found C, 51.77; H, 3.90; N, 8.43; F, 11.50. | 3382,1758, 1730,1723, 1680. | 2.06(s,3H),5.53(s,2H), 6.93–7.67(6H),7.7–8.3(1H). |
| 4. | (phenyl) | C$_2$H$_5$— | " | " | 78 | 89–90 | Calcd (for $C_{15}H_{15}O_5N_2F$) C, 55.90; H, 4.69; N, 8.69. Found C, 55.75; H, 4.48; N, 8.83. | 3375,1750, 1720,1710, 1672. | 1.06(6,J=7Hz,3H),2.30(q, J=7Hz,2H),5.55(s,2H), 7.15(d,J=5Hz,1H),7.20(s, 1H),7.40(5H),9.5–10.5 (br,1H). |
| 5. | (2-F-phenyl) | " | " | " | 70 | 111–112 | Calcd (for $C_{15}H_{14}O_5N_2F_2$) C, 52.94; H, 4.15; N, 8.23. Found C, 53.20; H, 4.25; N, 8.09. | 3380,1755, 1730,1725, 1675. | 1.05(t,J=7Hz,3H),2.30(q, J=7Hz,2H),5.53(s,2H), 7.83–6.87(6H),10.17(br, 1H). |
| 6 | (2-F-phenyl) | CH$_3$(CH$_2$)$_6$— | " | " | 23 | | | 3385,1755(sh), 1730,1717, 1675. | 0.85(t,J=5Hz,3H),1.0–1.8(10H),2.28(t,J=7Hz, 2H),5.57(s,2H),7.87–6.9(6H),10.66(br,1H). |
| 7 | (4-F-phenyl) | " | " | " | 21 | | | 3385,1755(sh), 1730,1715, 1675. | 0.85(t,J=5Hz,3H),1.0–1.87(10H),2.28(t,J=7Hz, 2H),5.53(s,2H),6.87–7.67(6H),10.3(br,1H). |
| 8 | (phenyl) | 1-adamantyl | " | " | 60 | 143–145 | Calcd (for $C_{23}H_{25}O_5N_2F$) C, 64.62; H, 5.90; N, 6.55. Found C, 64.67; H, 5.65; N, 6.45. | 3380,1730, 1713,1674. | 1.6–2.2(15H),5.56(s, 2H),7.15–7.25(2H), 7.43(5H),10.05–10.8 (1H). |
| 9 | (4-F-phenyl) | " | " | " | 16 | 161–163 | Calcd (for $C_{23}H_{24}O_5N_2F_2$) C, 61.87; H, 5.42; N, 6.28; F, 8.51. Found C, 61.30; H, 5.53; N, 7.02; F, 8.68. | 3380,1725, 1710,1670. | 1.3–2.0(15H),5.31(s, 2H),6.6–7.4(6H). |
| 10. | (phenyl) | (CH$_3$)$_3$C— | " | " | 55 | 133–135 | Calcd (for $C_{17}H_{19}O_5N_2F$) C, 58.78; H, 5.51; N, 8.07. Found C, 58.39; H, 5.69; N, 7.94. | 3375,1728, 1712,1672. | 1.13(s,9H),5.56(s,2H), 7.1–7.3(2H),7.43(s, 5H),8.9–9.6(br,1H). |

-continued

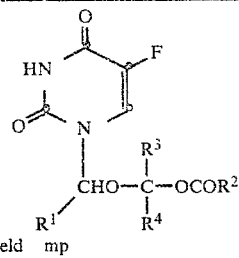

| No. | R¹ | R² | R³ | R⁴ | Yield (%) | mp (°C.) | Elemental Analysis | IR: $\nu_{max}^{CHCl_3}$(cm$^{-1}$) | NMR:$\delta^{CDCl_3}$ |
|---|---|---|---|---|---|---|---|---|---|
| 11. | (phenyl) | (CH₃)(CH₃)(CH₂)₅—C—CH₃ | " | " | 73.3 | 78–79 | Calcd (for C₂₂H₂₉O₅N₂F) C, 62.83; H, 6.95; N, 6.66; F, 4.51. Found C, 62.54; H, 7.27; N, 6.57; F, 4.71. | 3360,1722, 1708,1674. | 0.57–1.83(m,19H),5.53 (s,2H),7.10(d,J=4Hz,1H), 7.17(s,1H),7.38(s,5H), 10.03–10.77(br,1H). |
| 12 | HOOC—(phenyl)— | (CH₃)₃C— | " | " | 75.7 | 215–216 | Calcd (for C₁₈H₁₉O₇N₂F) C, 54.82; H, 4.84; N, 7.09; F, 4.81. Found C, 54.99; H, 5.09; N, 6.99; F, 4.96. | 3200–2400, 1745,1715, 1685. (Nujol) | 1.13(s,9H),5.58(s,2H), 7.15(s,1H),7.34(d,J=9Hz, 1H),7.45(d,J=6Hz,1H), 8.07(d,J=9Hz,1H). (d₆-DMSO) |

We claim:

1. A compound of the formula

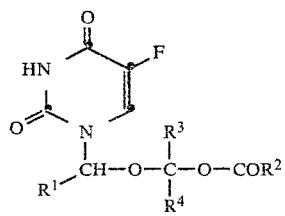

wherein

R¹ is $C_6$ to $C_{10}$ aryl or $C_6$ to $C_{10}$ aryl substituted by halogen, $C_1$ to $C_5$ alkyl, $C_1$ to $C_5$ haloalkyl, $C_1$ to $C_5$ alkoxy, nitro, cyano or carboxy, R² is $C_1$ to $C_{30}$ straight or branched chain alkyl, $C_3$ to $C_{11}$ cyclic alkyl wherein the cyclic moiety is 3 to 6 membered, adamantyl, $C_6$ to $C_{10}$ aryl or $C_6$ to $C_{10}$ aryl substituted by halogen, $C_1$ to $C_5$ alkyl, $C_1$ to $C_5$ haloalkyl, $C_1$ to $C_5$ alkoxy, nitro, cyano or carboxy, and R³ and R⁴ are the same or different and each is hydrogen or lower alkyl.

2. A compound claimed in claim 1, namely, 1-(α-acetoxymethoxybenzyl)-5-fluorouracil.

3. A compound claimed in claim 1, namely, 1-(α-acetoxymethoxy-2-fluorobenzyl)-5-fluorouracil.

4. A compound claimed in claim 1, namely, 1-(α-acetoxymethoxy-4-fluorobenzyl)-5-fluorouracil.

5. A compound claimed in claim 1, namely, 1-(α-propionyloxymethoxybenzyl)-5-fluorouracil.

6. A compound claimed in claim 1, namely, 1-(α-propionyloxymethoxy-2-fluorobenzyl)-5-fluorouracil.

7. A compound claimed in claim 1, namely, 1-(α-octanoyloxymethoxy-2-fluorobenzyl)-5-fluorouracil.

8. A compound claimed in claim 1, namely, 1-(α-octanoyloxymethoxy-4-fluorobenzyl)-5-fluorouracil.

9. A compound claimed in claim 1, namely, 1-[α-(1-adamantanoyloxymethoxy)benzyl]-5-fluorouracil.

10. A compound claimed in claim 1, namely, 1-[α-(1-adamantanoyloxymethoxy)-4-fluorobenzyl]-5-fluorouracil.

11. A compound claimed in claim 1, namely, 1-(α-pivaloyloxymethoxybenzyl)-5-fluorouracil.

12. A compound claimed in claim 1, namely, 1-[α-(2,2-dimethyloctanoyloxymethoxy)benzyl]-5-fluorouracil.

13. A compound claimed in claim 1, namely, 1-(α-pivaloyloxymethoxy-4-carboxybenzyl)-5-fluorouracil.

* * * * *